United States Patent [19]

Gaillard

[11] 4,417,091

[45] Nov. 22, 1983

[54] PROCESS FOR REMOVING FLUORINE FROM OLEFIN OLIGOMERS

[75] Inventor: Jean Gaillard, Lyons, France

[73] Assignee: Institut Francais du Petrole, Rueil-Malmaison, France

[21] Appl. No.: 373,182

[22] Filed: Apr. 29, 1982

[30] Foreign Application Priority Data

Apr. 29, 1981 [FR] France .................... 81 08760

[51] Int. Cl.³ .............................................. C07C 7/12
[52] U.S. Cl. ....................................... 585/823; 585/824; 585/842; 585/868; 208/262
[58] Field of Search ............... 585/823, 824; 208/262, 208/825, 826, 842, 868

[56] References Cited

U.S. PATENT DOCUMENTS

| | | | |
|---|---|---|---|
| 2,409,372 | 10/1946 | Matuszak | 208/262 |
| 2,628,933 | 2/1953 | Eagle et al. | 585/823 |
| 2,888,498 | 5/1959 | Carroll et al. | 585/823 |
| 3,238,268 | 3/1966 | Fenske | 585/823 |
| 3,331,881 | 7/1967 | Nixon et al. | 585/823 |
| 3,560,373 | 2/1971 | Washau et al. | 208/262 |
| 3,862,900 | 1/1975 | Reusser | 208/262 |
| 3,864,243 | 2/1975 | Reusser et al. | 208/262 |

*Primary Examiner*—Curtis R. Davis
*Assistant Examiner*—A Pal
*Attorney, Agent, or Firm*—Millen & White

[57] ABSTRACT

Fluorinated impurities are removed from olefin oligomers by extraction with a solid adsorbent; the oligomers have been obtained from monoolefins having 2–4 carbon atoms, in the presence of a catalyst obtained by contacting a bivalent nickel compound with a hydrocarbyl aluminum halide and a trifluoroacetic acid.

6 Claims, No Drawings

PROCESS FOR REMOVING FLUORINE FROM OLEFIN OLIGOMERS

BACKGROUND OF THE INVENTION

The object of the present invention is a process for removing fluorinated impurities from olefins.

The French Pat. No. 2,443,877 discloses an improved catalytic composition and its use as oligomerization catalyst for monoolefins, for example those having from 2 to 4 carbon atoms, and particularly as dimerization and/or trimerization catalyst therefor. This catalytic composition consists of the product obtained by contacting, in any order, a bivalent nickel compound with a hydrocarbyl aluminum halide and an organic Bronsted acid. The best results are obtained with the use, as Bronsted acid, of a halogenocarboxylic acid, for example trichloracetic acid or trifluoracetic acid. However an additional problem has appeared: all or part of the halogen is found in the resultant olefinic oligomerizate, which is unacceptable for a number of uses of this oligomerizate. The difficulty to remove the traces of halogen was then encountered. In view of the acidic nature of the halogenated compounds introduced into the catalyst, it could be expected that washing the oligomerizate with water or with an inorganic base such as sodium hydroxide, potassium hydroxide or ammonia in aqueous medium would remove these traces of halogen. The failure of this method shows that the halogen is no longer in the form of a halogenocarboxylic acid, that the problem has no obvious solution and that the halogen is probably found in the form of a compound soluble in hydrocarbons and which cannot be extracted easily.

SUMMARY OF THE INVENTION

It has been found surprisingly that these halogenated compounds can be removed by treating the hydrocarbon with a solid adsorbent, for example an inorganic solid adsorbent such as silica, alumina, silica-alumina or activated earths. This adsorbent is preferably used in a substantially dehydrated form, although traces of water can be tolerated. The dehydration can be performed by different methods, for example by heating.

DETAILED DISCUSSION

The invention is not limited to the treatment of a mixture of olefins obtained by oligomerization. It applies in all cases where a hydrocarbon contains, in solution, a halogenated compound which cannot be extracted with water or with an aqueous base.

According to the invention, the olefins mixture containing halogenated compounds is treated with the adsorbent in fluid bed or preferably percolated through a column containing said adsorbent. The volumes of hydrocarbons to be used are from 1 to 10,000 times, preferably 3 to 1000 times the volume of the inorganic adsorbent. The flow rate is, for example, from 0.1 to 100 and preferably from 1 to 25 volumes of hydrocarbons per volume of adsorbent per hour. The operating temperature is, for example, from −20° C. to +80° C., preferably from +10° C. to +60° C.

When the adsorbent is saturated with the halogen compound, thus when the effluent has the same halogen content as the feed charge, the operation is stopped and the adsorbent is regenerated, for example by heating in a stream of inert gas, for example a stream of nitrogen or steam, or by passing a hydrocarbon therethrough. The regeneration temperature is usually between 100° C. and 350° C., preferably between 150° and 250° C. A dry inert gas is preferably used. After regeneration, the adsorbent is ready for re-use.

The following examples illustrate the invention without limiting the scope thereof.

Example 1

The oligomerization of a halogen-free butenes cut, by means of a catalytic system formed by reacting nickel heptanoate with dichloroethylaluminum and trifluoracetic acid has lead to a mixture of oligomers whose trimeric fraction contains 250 parts per million by weight of fluorine. 100 ml of this fraction are percolated at room temperature, in one hour, through 27 g of silica gel of the Grace 123 type, previously heated to 150° C. in a dry nitrogen stream. After treatment, the trimeric fraction contains less than 5 parts per million by weight of fluorine.

Silica gel is then heated to 200° C. and can be re-used for a second purification.

What is claimed is:

1. A process for removing fluorine from a liquid olefin or from a liquid olefinic cut obtained by dimerizing or trimerizing at least one monoolefin having from 2 to 4 carbon atoms, in the presence of a catalyst obtained by contacting a bivalent nickel compound with a hydrocarbyl aluminum halide and trifluoroacetic acid, said process comprising percolating said olefin or olefinic cut through silica gel at an hourly flow rate of 0.1 to 100 volumes of said olefin or olefinic cut per volume of said silica gel and at a temperature of from −20° to +80° C.

2. A process according to claim 1, wherein the proportion of the adsorbent is from 0.0001 to 1 part by weight of the olefin or the olefinic cut.

3. A process according to claim 1, wherein the hourly flow rate is 1–25 volumes of said olefin or olefinic cut per volume of silica gel and the temperature is from +10° to +60° C.

4. A process according to claim 1, which further comprises regenerating the spent silica gel by heating at 100°–350° C. in a stream of inert gas.

5. A process according to claim 4, wherein said inert gas is dry nitrogen.

6. A process according to claim 4, wherein the regeneration is effected at 150°–250° C.

* * * * *